(12) United States Patent
Plahey et al.

(10) Patent No.: US 9,579,443 B2
(45) Date of Patent: Feb. 28, 2017

(54) PERITONEAL DIALYSIS SYSTEMS AND RELATED DEVICES AND METHODS

(71) Applicant: Fresenius Medical Care Holdings, Inc., Waltham, MA (US)

(72) Inventors: Kulwinder S. Plahey, Martinez, CA (US); Sean Farrell, Walnut Creek, CA (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 718 days.

(21) Appl. No.: 13/738,144

(22) Filed: Jan. 10, 2013

(65) Prior Publication Data

US 2014/0194809 A1  Jul. 10, 2014

(51) Int. Cl.
*A61M 1/28* (2006.01)
*A61M 1/14* (2006.01)
*A61M 1/16* (2006.01)

(52) U.S. Cl.
CPC ............... *A61M 1/28* (2013.01); *A61M 1/282* (2014.02); *A61M 1/14* (2013.01); *A61M 1/16* (2013.01);
(Continued)

(58) Field of Classification Search
CPC ..... A61M 1/28; A61M 1/282; A61M 2205/12; A61M 2205/128; A61M 1/16; A61M 1/14
See application file for complete search history.

(56) References Cited

U.S. PATENT DOCUMENTS 5,324,422 A * 6/1994 Colleran ............... A61M 1/28
                                                    210/143
5,643,201 A * 7/1997 Peabody ............... A61M 1/28
                                                    604/29
(Continued)

FOREIGN PATENT DOCUMENTS

CN     101175514 A    5/2005
EP      1904122 A1    4/2008
(Continued)

OTHER PUBLICATIONS

Kaldoudi et al., "Homecare Telematics for Peritoneal Dialysis", The Journal of Information Technology in Healthcare, 2007, vol. 5, No. 6, pp. 372-378.

(Continued)

*Primary Examiner* — Imani Hayman
*Assistant Examiner* — Nilay Shah
(74) *Attorney, Agent, or Firm* — Fish & Richardson P.C.

(57) ABSTRACT

A peritoneal dialysis system includes a base peritoneal dialysis system and a peritoneal dialysis fluid exchange system that operates independently of the base system. The base system includes a first cassette including a first patient line configured to be connected to a patient, and a PD cycler. The PD cycler receives the first cassette, and includes a pump that cooperates with the first cassette to deliver dialysate to and drain dialysate from a peritoneal cavity of the patient via the first patient line. The peritoneal dialysis fluid exchange system includes a second cassette including a second patient line configured to be connected to the patient and a fluid exchange device that receives the second cassette. The fluid exchange device includes a data exchange interface operable to transfer patient treatment data from the peritoneal dialysis fluid exchange system to the base peritoneal dialysis system.

19 Claims, 10 Drawing Sheets

(52) U.S. Cl.
CPC ... *A61M 2205/12* (2013.01); *A61M 2205/128* (2013.01); *A61M 2205/3331* (2013.01); *A61M 2205/3334* (2013.01); *A61M 2205/3561* (2013.01); *A61M 2205/3576* (2013.01); *A61M 2205/52* (2013.01)

(56) References Cited

U.S. PATENT DOCUMENTS

| | | |
|---|---|---|
| 5,670,057 A | 9/1997 | Chen et al. |
| 5,783,072 A | 7/1998 | Kenley et al. |
| 6,081,786 A | 6/2000 | Barry et al. |
| 6,615,074 B2 | 9/2003 | Mickle et al. |
| 6,673,314 B1 | 1/2004 | Burbank et al. |
| 6,746,398 B2 | 6/2004 | Hervy et al. |
| 6,780,322 B1 | 8/2004 | Bissler et al. |
| 6,835,175 B1 | 12/2004 | Porumbescu |
| 6,913,590 B2 | 7/2005 | Sorenson et al. |
| 6,979,309 B2 | 12/2005 | Burbank et al. |
| 7,044,002 B2 * | 5/2006 | Ericson ............ A61M 5/16804 604/65 |
| 7,153,286 B2 | 12/2006 | Busby et al. |
| 7,433,853 B2 | 10/2008 | Brockway et al. |
| 7,699,806 B2 | 4/2010 | Ware et al. |
| 7,785,463 B2 | 8/2010 | Bissler et al. |
| 7,801,591 B1 | 9/2010 | Shusterman |
| 7,815,595 B2 | 10/2010 | Busby et al. |
| 7,852,208 B2 | 12/2010 | Collins et al. |
| 7,859,401 B2 | 12/2010 | Falck et al. |
| 7,887,502 B2 | 2/2011 | Ross et al. |
| 7,918,993 B2 | 4/2011 | Harraway |
| 8,057,679 B2 | 11/2011 | Yu et al. |
| 8,066,671 B2 | 11/2011 | Busby et al. |
| 8,075,526 B2 | 12/2011 | Busby et al. |
| 8,095,390 B2 | 1/2012 | Bluemler et al. |
| 8,206,338 B2 | 6/2012 | Childers et al. |
| 8,262,602 B2 | 9/2012 | Lee et al. |
| 8,282,829 B2 | 10/2012 | Yu et al. |
| 8,313,642 B2 | 11/2012 | Yu et al. |
| 8,777,893 B2 | 7/2014 | Malewicz et al. |
| 8,882,700 B2 | 11/2014 | Chapman et al. |
| 2001/0007058 A1 | 7/2001 | Jonsson et al. |
| 2003/0065409 A1 | 4/2003 | Raeth et al. |
| 2005/0010216 A1 | 1/2005 | Gradel et al. |
| 2005/0256745 A1 | 11/2005 | Dalton |
| 2006/0015015 A1 | 1/2006 | Kawamoto et al. |
| 2006/0084906 A1 | 4/2006 | Burbank et al. |
| 2006/0154642 A1 | 7/2006 | Scannell |
| 2008/0097283 A1 | 4/2008 | Plahey |
| 2008/0161751 A1 | 7/2008 | Plahey et al. |
| 2008/0285626 A1 | 11/2008 | Claus et al. |
| 2008/0312960 A1 | 12/2008 | Nikolic et al. |
| 2009/0076856 A1 | 3/2009 | Darby et al. |
| 2009/0078622 A1 | 3/2009 | Zhang et al. |
| 2009/0101550 A1 * | 4/2009 | Muller ................... A61M 1/16 210/87 |
| 2009/0299273 A1 * | 12/2009 | Lee ......................... A61M 1/28 604/29 |
| 2009/0306573 A1 | 12/2009 | Gagner et al. |
| 2010/0298662 A1 * | 11/2010 | Yu ........................... A61M 1/28 600/301 |
| 2010/0312174 A1 | 12/2010 | Hoffman |
| 2011/0071465 A1 | 3/2011 | Wang et al. |
| 2011/0184340 A1 | 7/2011 | Tan et al. |
| 2012/0029325 A1 | 2/2012 | Neftel |
| 2012/0035534 A1 | 2/2012 | Yu et al. |
| 2012/0271226 A1 | 10/2012 | Farrell et al. |
| 2012/0302844 A1 * | 11/2012 | Schnidrig ............ A61B 5/6833 600/309 |

FOREIGN PATENT DOCUMENTS

| | | |
|---|---|---|
| WO | WO03099354 A2 | 12/2003 |
| WO | WO2005035023 A1 | 4/2005 |
| WO | WO2007126360 A1 | 11/2007 |
| WO | WO2011046797 A1 | 4/2011 |

OTHER PUBLICATIONS

Nakamoto et al., "Telemedicine System for Home Automated Peritoneal Dialysis", http://www,advancesinpd.com/adv00/Telemedicine00.html, retrieved from the web [Dec. 11, 2012], 5 pages.

Nakamoto, Hidetomo, "Telemedicine System for Patients on Continuous Ambulatory Peritoneal Dialysis", Proceedings of the ISPD 2006—the 11th Congress of the ISPD, Aug. 25-29, 2006, Hong Kong, Peritoneal Dialysis International, vol. 27, (2007), Supplement 2, 6 pages.

Pieper et al., "Chapter 9: Patients and EHRs Tele Home Monitoring Reference Scenario", C. Stephanidis (Ed.): Universal Access Code of Practice in Health Telematics, LNCS 3041, pp. 77-87, 2005.

Search Report for Invalidity Search against US20120035534 Relating to Dialysis Machines with Wireless Communication, Global Prior Art, Inc., Boston, MA, Sep. 17, 2012, 3 pages.

Patentability Search Report, "Daytime Exchange Assistant", ip.com, Mar. 14, 2012, 22 pages.

Notification of Transmittal of the International Search Report and the Written Opinion of the International Search Authority from corresponding PCT Application No. PCT/US2013/077424, mailed Jul. 22, 2014, 18 pages.

Annex to Form PCT/ISA/206—Communication Relating to the Results of the Partial International Search for corresponding PCT Application No. PCT/US2013/077424, mailed Apr. 4, 2014, 8 pages.

Dialease—The Future of Home Dialysis, http://www.debiotech.com/products/eleinfsys/disease_page_1..html, retrieved from the web Nov. 2, 2012, 9 pages.

Notification Concerning Transmittal of International Preliminary Report on Patentability Written Opinion of the International Search Authority from corresponding PCT Application No. PCT/US2013/077424, mailed Jul. 23, 2015, 12 pages.

* cited by examiner

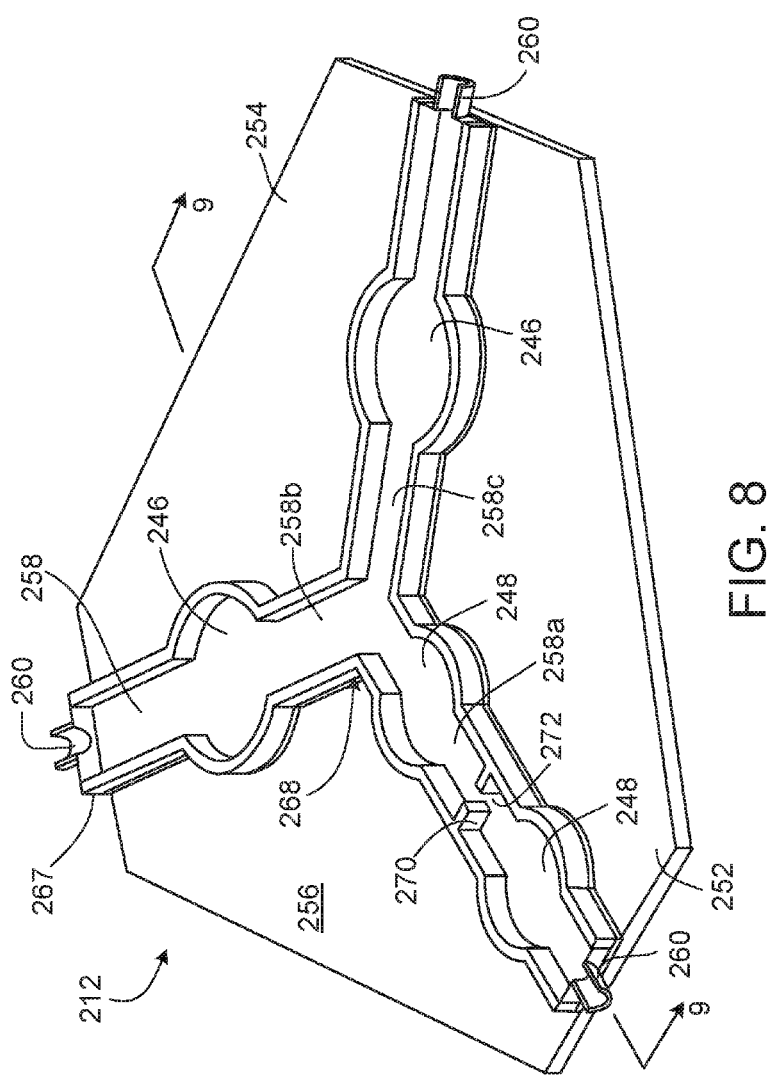
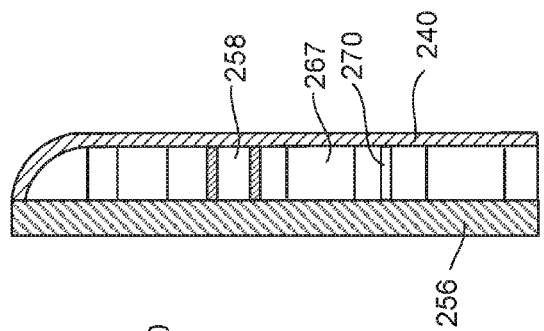
FIG. 8
FIG. 9

PERITONEAL DIALYSIS SYSTEMS AND RELATED DEVICES AND METHODS

TECHNICAL FIELD

This disclosure relates to peritoneal dialysis systems and related devices and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Many PD machines, commonly referred to as "cyclers", are designed to automatically infuse, dwell, and drain dialysate to and from the patient's peritoneal cavity in a process referred to as "continuous cycler-assisted peritoneal dialysis" (CCPD). The treatment typically lasts for several hours, often beginning with an initial drain procedure to empty the peritoneal cavity of used or spent dialysate. The sequence then proceeds through the succession of infusion, dwell, and drain phases that follow one after the other. Each phase is called a cycle.

Due to the length of the treatment, the large size of the PD machine and the large volume of dialysate required for the treatment, the treatment may be performed at home while the patient sleeps. Although nighttime CCPD treatments are sufficient for some patients, other patients require one or more additional fluid exchanges during the daytime. To permit the patient to participate in normal daily activities outside of the home, continuous ambulatory peritoneal dialysis (CAPD) is performed by connecting a bag of dialysis fluid to the patient's peritoneal catheter, and delivering about 1-3 liters of dialysate to the peritoneal cavity. After permitting the dialysate to dwell in the peritoneal cavity for a predetermined period of time, the dialysate is drained from the peritoneal cavity. The patient typically monitors and records the number of daytime exchanges and the amounts of dialysate used during the daytime exchanges.

SUMMARY

In one aspect, a peritoneal dialysis system includes a base peritoneal dialysis system and a peritoneal dialysis fluid exchange system that operates independently of the base peritoneal dialysis system. The base peritoneal dialysis system includes a first disposable unit including a first patient line configured to be connected to a patient, and a peritoneal dialysis device. The peritoneal dialysis device includes a compartment configured to receive the first disposable unit, and at least one pump arranged so that when the first disposable unit is disposed within the compartment. The pump cooperates with the first disposable unit to deliver dialysate to and drain dialysate from a peritoneal cavity of the patient via the first patient line of the first disposable unit. The peritoneal dialysis fluid exchange system includes a second disposable unit including a second patient line configured to be connected to the patient such that fluid can be delivered to and drained from the peritoneal cavity of the patient via the second patient line, and a fluid exchange device. The fluid exchange device includes a compartment configured to receive the second disposable unit, and a data exchange interface operable to transfer patient treatment data from the peritoneal dialysis fluid exchange system to the base peritoneal dialysis system.

Implementations can include one or more of the following features:

In some implementations, the base peritoneal dialysis system is configured to automatically deliver dialysate to and automatically drain dialysate from a peritoneal cavity of a patient based on a patient treatment plan, and modify the patient treatment plan based on the patient treatment data transferred from the peritoneal dialysis fluid exchange system.

In some implementations, the data exchange interface is a transmitter, and the base peritoneal dialysis system further comprises a receiver.

In some implementations, the data exchange interface is an input/output port configured to permit connection to a data communication line extending from the base peritoneal dialysis system.

In some implementations, the peritoneal dialysis fluid exchange system comprises a fluid flow meter.

In some implementations, the fluid exchange device further comprises a sensor disposed adjacent to the second disposable unit when the second disposable unit is disposed in the compartment of the fluid exchange device, the sensor being operable to obtain the patient treatment data.

In some implementations, the patient treatment data includes a volume of fluid transferred to the patient and a volume of fluid drained from the patient.

In some implementations, the peritoneal dialysis fluid exchange system includes a processor configured to calculate fluid flow rates through the peritoneal dialysis fluid exchange system, calculate the duration of fluid flow through the peritoneal dialysis fluid exchange system, and use the calculated fluid flow rates and calculated duration to determine at least one of a volume of fluid infused to the patient and a volume of fluid drained from the patient.

In some implementations, the processor is further configured to store at least one of the calculated fluid flow rates, calculated duration, volume of fluid transferred to the patient and a volume of fluid drained from the patient.

In some implementations, the second disposable unit comprises a base, and a flexible membrane attached to the base in such a way that the base and the flexible membrane cooperate to form a fluid passageway that can be placed in communication with the second patient line, wherein the fluid passageway includes a first pressure sensor seat, a second pressure sensor seat, and a localized region of reduced fluid passageway diameter disposed between the first pressure sensor seat and the second pressure sensor seat.

In some implementations, the second disposable unit comprises a base, and a flexible membrane attached to the base in such a way that the base and the flexible membrane cooperate to form a fluid passageway that can be placed in communication with the second patient line. The second patient line has a patient line portion connected to an infusion line portion and a drain line portion, and the patient line portion includes a first pressure sensor seat, a second pressure sensor seat, and a localized region of reduced fluid passageway diameter disposed between the first pressure sensor seat and the second pressure sensor seat.

In some implementations, the fluid exchange device includes a first pressure sensor and a second pressure sensor, the fluid exchange device is configured to receive the second disposable unit within the fluid exchange device compartment in a manner such that the first pressure sensor is disposed at a location corresponding to the first pressure sensor seat, and the second pressure sensor is disposed at a location corresponding to the second pressure sensor seat, and the fluid exchange device further includes a controller. The controller is configured to receive fluid pressure data detected by the first pressure sensor and the second pressure sensor, and calculate fluid flow data based on the received fluid pressure data, and transmit the fluid flow data to the data exchange interface.

In some implementations, the infusion line portion includes an infusion line portion valve seat and the drain line portion includes a drain line portion valve seat. In addition, the second disposable unit includes a pump chamber disposed between the first pressure sensor seat and a region in which the infusion line portion and the drain line portion connect to the patient line portion. The fluid exchange device is configured to receive the second disposable unit within the fluid exchange device compartment in a manner such that an infusion line valve is disposed at a location corresponding to the infusion line portion valve seat, a drain line valve is disposed at a location corresponding to the drain line portion valve seat, and a fluid pump is disposed at a location corresponding to the pump chamber, the fluid pump configured to cooperate with the pump chamber to pump fluid within the fluid passageway.

In some implementations, the infusion line portion includes an infusion line portion valve seat and the drain line portion includes a drain line portion valve seat. In addition, the second disposable unit includes a pump chamber disposed between the first pressure sensor seat and a region in which the infusion line portion and the drain line portion connect to the patient line portion, and a pump rotor disposed within the pump chamber. The fluid exchange device is configured to receive the second disposable unit within the fluid exchange device compartment in a manner such that an infusion line valve is disposed at a location corresponding to the infusion line portion valve seat, a drain line valve is disposed at a location corresponding to the drain line portion valve seat, and an induction coil is disposed at a location corresponding to the pump chamber, the induction coil configured to drive the pump rotor to pump fluid within the fluid passageway.

In some implementations, the second disposable unit comprises a bypass passageway that selectively permits fluid flow to be diverted past the pump chamber.

In some implementations, the second disposable unit comprises a bypass passageway including a first end that communicates with the patient line portion at a location between the pump chamber and the region in which the infusion line portion and the drain line portion connect to the patient line portion, a second end that communicates with the patient line portion at a location between the pump chamber and the first pressure sensor seat, and a bypass valve seat.

In some implementations, the fluid exchange device comprises a bypass valve at a location corresponding to the bypass valve seat.

In some implementations, the localized region of reduced fluid passageway diameter includes an orifice plate disposed in the fluid passageway, the orifice plate including an opening having a smaller diameter than the inner diameter of portions of the fluid passageway on either side of the orifice plate.

In some implementations, the transferred patient treatment data is synchronized with patient treatment data of the base peritoneal dialysis system.

In some implementations, the peritoneal dialysis fluid exchange system has a size and a weight that are less than the size and the weight of the base peritoneal dialysis system.

In some implementations, the peritoneal dialysis fluid exchange system has a weight that is less than 1 lb.

In another aspect, a peritoneal dialysis device includes a compartment configured to receive a disposable unit that includes a patient line configured to be connected to a patient, at least one pump arranged so that when the disposable unit is disposed within the compartment, the pump cooperates with the disposable unit to deliver dialysate to and drain dialysate from a peritoneal cavity of the patient via the patient line of the disposable unit in accordance with a patient treatment plan, a data transfer interface configured to receive patient treatment data from an independent peritoneal dialysis system, the patient data having been obtained during peritoneal dialysis performed by the independent peritoneal dialysis system, and a controller that automatically modifies the patient treatment plan based on the received patient treatment data.

In another aspect, a method of providing dialysis treatment includes obtaining patient treatment data during peritoneal dialysis performed by a first peritoneal dialysis system, transferring the obtained patient treatment data from the first peritoneal dialysis system to a second peritoneal dialysis system, and determining a modified patient treatment plan using the second peritoneal dialysis system based on the obtained patient treatment data transferred from the first peritoneal dialysis system, the modified patient treatment plan to be carried out by the second peritoneal dialysis system.

Implementations can include one or more of the following features:

In some implementations, the method includes performing peritoneal dialysis using the second peritoneal dialysis system based on the modified patient treatment plan.

In some implementations, obtaining the patient treatment data includes measuring fluid flow rates through the first peritoneal dialysis system and measuring fluid flow durations through the first peritoneal dialysis system.

In some implementations, obtaining the patient treatment data includes measuring fluid flow rates through the first peritoneal dialysis system and measuring fluid flow durations through the first peritoneal dialysis system, and using the measured fluid flow rates and measured fluid flow durations to determine at least one of a volume of fluid infused to the patient and a volume of fluid drained from the patient.

In some implementations, determining the modified patient treatment plan includes adjusting at least one of an infusing volume and a draining volume in a dialysis treatment based on the volume of fluid infused to the patient and a volume of fluid drained from the patient using the first peritoneal dialysis system.

In some implementations, transferring the obtained patient treatment data is achieved via a wireless connection between the first peritoneal dialysis system and the second peritoneal dialysis system.

In some implementations, transferring the obtained patient treatment data is achieved via a wired connection between the first peritoneal dialysis system and the second peritoneal dialysis system.

In other aspects, a peritoneal dialysis cassette includes a base, and a flexible membrane attached to the base in such a way that the base and the flexible membrane cooperate to form a fluid passageway, the fluid passageway having a patient line portion connected to an infusion line portion and a drain line portion. The fluid passageway includes a first pressure sensor seat, a second pressure sensor seat, and a localized region of reduced fluid passageway diameter disposed between the first pressure sensor seat and the second pressure sensor seat.

Implementations can include one or more of the following features.

In some implementations, the peritoneal dialysis cassette includes a pump chamber disposed along the fluid passageway between the first pressure sensor seat and a region in which the infusion line portion and the drain line portion connect to the patient line portion.

In some implementations, the peritoneal dialysis cassette includes an induction pump at least partially disposed within the pump chamber.

In some implementations, the peritoneal dialysis cassette includes a bypass passageway that selectively permits fluid flow to be diverted past the pump chamber.

In some implementations, the peritoneal dialysis cassette includes a bypass passageway including a first end that communicates with the patient line portion at a location between the pump chamber and the region in which the infusion line portion and the drain line portion connect to the patient line portion, a second end that communicates with the patient line portion at a location between the pump chamber and the first pressure sensor seat, and a bypass valve seat.

In some implementations, the localized region includes an orifice plate disposed in the fluid passageway, the orifice plate including an opening having a smaller diameter than the inner diameter of portions of the fluid passageway on either side of the orifice plate.

In other aspects, a peritoneal dialysis system includes a peritoneal dialysis cassette including a base, and a flexible membrane attached to the base in such a way that the base and the flexible membrane cooperate to form a fluid passageway, the fluid passageway having a patient line portion connected to an infusion line portion and a drain line portion. The fluid passageway includes a first pressure sensor seat, a second pressure sensor seat, and a localized region of reduced fluid passageway diameter disposed between the first pressure sensor seat and the second pressure sensor seat.

Implementations can include one or more of the following features.

In some implementations, the system further comprises a fluid exchange device that includes a first pressure sensor and a second pressure sensor. The fluid exchange device is configured to support the cassette in a manner such that the first fluid pressure sensor is disposed at a location corresponding to the first pressure sensor seat, and the second fluid pressure sensor is disposed at a location corresponding to the second pressure sensor seat. The fluid exchange device further includes a controller that is configured to receive fluid pressure data detected by the first fluid pressure sensor and the second fluid pressure sensor, and calculate fluid flow data based on the received fluid pressure data, and a data exchange interface that is configured to transmit fluid flow data to a location remote from the peritoneal dialysis device.

In some implementations, the infusion line portion includes an infusion line portion valve seat, the drain line portion includes a drain line portion valve seat, and the peritoneal dialysis cassette includes a pump chamber disposed between the first pressure sensor seat and a region in which the infusion line portion and the drain line portion connect to the patient line portion. In addition, the fluid exchange device includes an infusion line valve at a location corresponding to the infusion line portion valve seat, a drain line valve at a location corresponding to the drain line portion valve seat, and a fluid pump at a location corresponding to the pump chamber, the fluid pump configured to cooperate with the pump chamber to pump fluid through the fluid passageway.

In some implementations, the infusion line portion includes an infusion line portion valve seat, the drain line portion includes a drain line portion valve seat, and the peritoneal dialysis cassette further includes a pump chamber disposed between the first pressure sensor seat and a region in which the infusion line portion and the drain line portion connect to the patient line portion, and a pump rotor disposed within the pump chamber. In addition, the fluid exchange device includes an infusion line valve at a location corresponding to the infusion line portion valve seat, a drain line valve at a location corresponding to the drain line portion valve seat, and an induction coil at a location corresponding to the pump chamber, the induction coil configured to drive the pump rotor to pump fluid through the fluid passageway.

In some implementations, the peritoneal dialysis cassette further comprises a bypass passageway that selectively permits fluid flow to be diverted past the pump chamber.

In some implementations, the peritoneal dialysis cassette further comprises a bypass passageway including a first end that communicates with the patient line portion at a location between the pump chamber and the region in which the infusion line portion and the drain line portion connect to the patient line portion, a second end that communicates with the patient line portion at a location between the pump chamber and the first pressure sensor seat, and a bypass valve seat.

In some implementations, the fluid exchange device includes a bypass valve at a location corresponding to the bypass valve seat.

In some implementations, the localized region of reduced fluid passageway diameter includes an orifice plate disposed in the fluid passageway, the orifice plate including an opening having a smaller diameter than the inner diameter of portions of the fluid passageway on either side of the orifice plate.

Implementations can include one or more of the following advantages:

In some implementations, a peritoneal dialysis fluid exchange system permits CAPD while automatically measuring and recording the amount of fluid exchanged during the CAPD. For example, the peritoneal dialysis fluid exchange system determines the volume of fluid delivered to the peritoneal cavity and the volume of fluid drained from the peritoneal cavity during the CAPD. Since the peritoneal dialysis fluid exchange system automatically measures and records the amount of fluid exchanged during the CAPD, patient errors and measurement inaccuracies during data collection can be avoided.

In some implementations, the peritoneal dialysis fluid exchange system includes a small, light-weight (e.g., hand-held) machine and a disposable fluid line set that is received within the machine. The peritoneal dialysis fluid exchange system is more portable than some conventional PD cyclers, and therefore is more convenient for daytime fluid exchanges that typically occur away from home.

In some implementations, the peritoneal dialysis fluid exchange system includes a fluid pump and valves permitting improved control of dialysate flow during CAPD. Using the peritoneal dialysis fluid exchange system to perform CAPD can reduce the time required to perform fluid delivery to and drain fluid from the peritoneal cavity during CAPD, and help to ensure that all delivered fluid is subsequently drained during each CAPD cycle.

In some implementations, a peritoneal dialysis system includes a base PD system that performs CCPD in accordance with a patient treatment plan, and a peritoneal dialysis fluid exchange system that performs CAPD at a location remote from the base PD system. The peritoneal dialysis fluid exchange system automatically measures and records patient treatment data including the amount of fluid exchanged during the CAPD, and automatically transfers the patient treatment data to the base PD system. Upon receipt of the transferred patient treatment data, the base PD system updates and modifies the patient treatment plan, and performs peritoneal dialysis based on the modified patient treatment plan. Since the peritoneal dialysis fluid exchange system transfers the patient treatment data obtained during CAPD to the base PD system, the quality of the CCPD performed by the base PD system is improved because the patient treatment plan is performed with more accuracy. In addition, there is reduced opportunity for human error during collection of patient treatment data during CAPD and transfer of the collected patient treatment data to the PD system. Other benefits include a reduced likelihood of chances of patient overfill during CCPD since daytime exchange volumes are automatically measured and recorded by the peritoneal dialysis fluid exchange system, transferred to the base PD system, and the patient treatment plan performed by the base PD system is modified to reflect the transferred data.

Other aspects, features, and advantages will be apparent from the description and drawings, and from the claims.

DESCRIPTION OF DRAWINGS

FIG. 8 is a perspective view of the PD fluid exchange cassette of FIG. 5.

FIG. 9 is a side sectional view of the PD fluid exchange cassette of FIG. 5 as seen along line 9-9 of FIG. 8.

DETAILED DESCRIPTION

Figure 1:
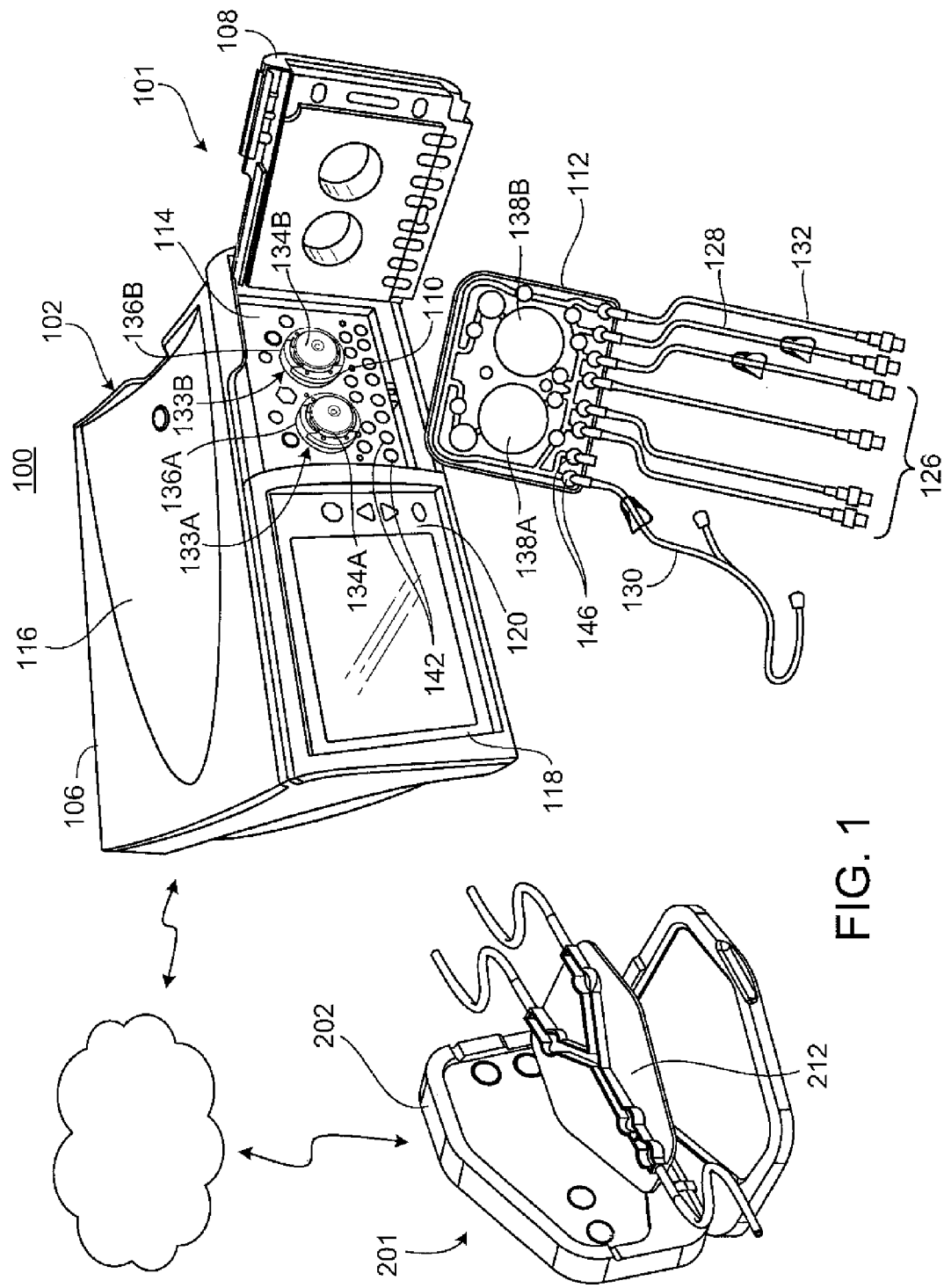
FIG. 1 is a perspective view of a peritoneal dialysis ("PD") system that includes a PD cycler and a PD fluid exchange device that can transmit data to the PD cycler.
Figure 2:
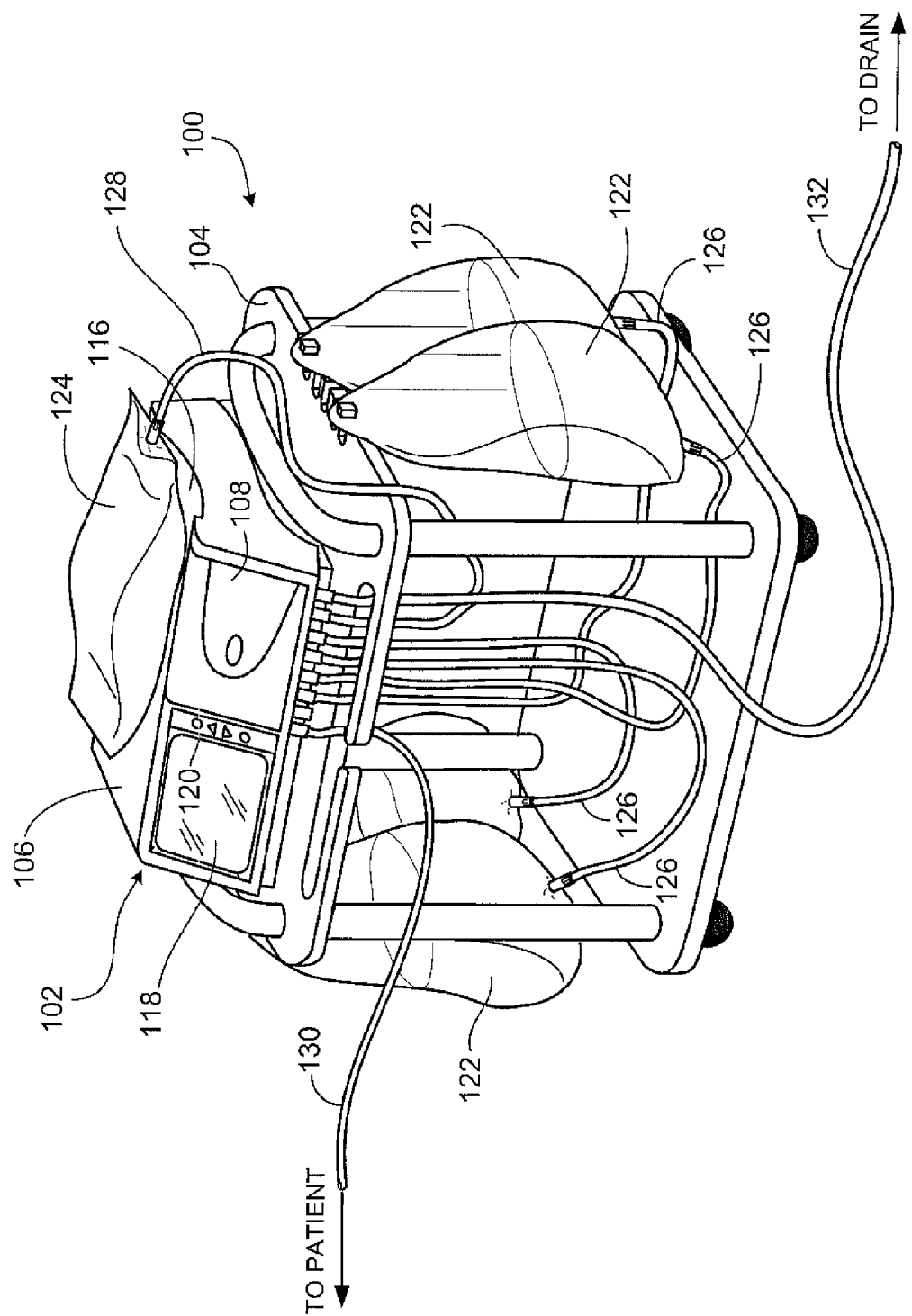
FIG. 2 is a perspective view of the PD cycler of FIG. 1 positioned atop a portable cart.

Referring to FIGS. 1 and 2, a peritoneal dialysis ("PD") system includes a base PD system 101, and a peritoneal dialysis fluid exchange system 201. The peritoneal dialysis fluid exchange system 201 operates independently of the base PD system 101, and during operation may be physically remote from the base PD system 101. For example, in some embodiments, the peritoneal dialysis fluid exchange system is used to provide a daytime fluid exchange as a part of CAPD at work or school. The peritoneal dialysis fluid exchange system includes a peritoneal dialysis fluid exchange device (e.g., a PD fluid exchange device) 202 and a simplified medical fluid cassette (e.g. a fluid exchange cassette) 212. The PD fluid exchange device 202 is small and light-weight relative to the PD cycler 102 such that it can be easily transported. In some cases, the PD fluid exchange device 202 is sized to be hand-held. In addition, the PD fluid exchange device 202 includes detectors that monitor and record patient treatment data including fluid flow rates, and a data exchange interface operable to transfer the patient treatment data obtained by the PD fluid exchange device 202 to the PD cycler 102, as discussed in more detail below.

The base PD system 101 includes the PD cycler 102 and a disposable PD fluid cassette 112 such as that described in co-pending U.S. patent application Ser. No. 13/442,184 filed on Apr. 9, 2012 and incorporated by reference herein. In some embodiments, the PD cycler 102 and PD cassette 112 are used to provide continuous cycler-assisted peritoneal dialysis. As such, the PD cycler (also referred to as a PD machine) 102 is designed for home use. Due to its size and weight, the PD cycler 102 is illustrated as being supported on a cart 104 that is used to improve ease of handling and storage of the PD cycler 102 in the home environment. The PD cycler 102 includes a housing 106, a door 108, and a cassette interface 110 that abuts the disposable PD fluid cassette 112 when the PD fluid cassette 112 is disposed within a cassette compartment 114 formed between the cassette interface 110 and the closed door 108. A heater tray 116 is positioned on top of the housing 106. The heater tray 116 is sized and shaped to accommodate a bag of dialysis solution (e.g., a 5 liter bag of dialysis solution). The PD cycler 102 also includes a display screen 118 and control buttons 120. In some embodiments, the display screen 118 is a touch screen. The display screen 118 and control buttons 120 can be operated by a user (e.g., a patient) to allow, for example, set-up, initiation, and/or termination of a PD treatment.

Dialysis solution bags 122 are suspended from fingers on the sides of the cart 104, and a heater bag 124 is positioned on the heater tray 116, as shown in FIG. 2. The dialysis solution bags 122 and the heater bag 124 are connected to the cassette 112 via dialysis solution bag lines 126 and a heater bag line 128, respectively. The dialysis solution bag lines 126 can be used to pass dialysis solution from dialysis solution bags 122 to the cassette 112 during use, and the heater bag line 128 can be used to pass dialysis solution back and forth between the cassette 112 and the heater bag 124 during use. In addition, a patient line 130 and a drain line 132 are connected to the cassette 112. The patient line 130 can be connected to a patient's abdomen via a catheter and can be used to pass dialysis solution back and forth between the cassette 112 and the patient during use. The drain line 132 can be connected to a drain or drain receptacle and can be used to pass dialysis solution from the cassette 112 to the drain or drain receptacle during use.

The PD cycler 102 includes pistons 133A, 133B with piston heads 134A, 134B that can be axially moved within piston access ports 136A, 136B formed in the cassette interface 110. The pistons 133A, 133B are connected to motors that can be operated to move the piston heads 134A, 134B axially inward and outward within the piston access ports 136A, 136B. As discussed below, when the cassette 112 is positioned within the cassette compartment 114 of the PD cycler 102 with the door 108 closed, the piston heads 134A, 134B of the PD cycler 102 align with pump chambers 138A, 138B of the cassette 112 such that the piston heads 134A, 134B can be mechanically connected to dome shaped fastening members 161A, 161B of the cassette 112 overlying the pump chambers 138A, 138B. As a result of this arrangement, movement of the piston heads 134A, 134B toward the cassette 112 during treatment can decrease the volume of the pump chambers 138A, 138B, and force dialysis solution out of the pump chambers 138A, 138B, while retraction of the piston heads 134A, 134B away from the cassette 112 can increase the volume of the pump chambers 138A, 138B and cause dialysis solution to be drawn into the pump chambers 138A, 138B. Thus, the motors, pistons 133A, 133B, and piston heads 134A, 134B serve as a fluid pump 150 that, in cooperation with the pump chambers 138A, 138B, drives fluid through the PD cassette 112.

The PD cycler 102 also includes multiple inflatable members 142 positioned within inflatable member ports in the cassette interface 110. The inflatable members 142 align with depressible dome regions 146 of the cassette 112 when the cassette 112 is positioned within the cassette compartment 114 of the PD cycler 102. While only two of the inflatable members 142 and dome regions 146 are labeled in FIG. 1, it should be understood that the PD cycler 102 includes an inflatable member associated with each of the depressible dome regions 146 of the cassette 112. The inflatable members 142 act as valves to direct dialysis solution through the cassette 112 in a desired manner during use. In particular, the inflatable members 142 bulge outward beyond the surface of the cassette interface 110 and into contact with the depressible dome regions 146 of the cassette 112 when inflated, and retract into the inflatable member ports and out of contact with the cassette 112 when deflated. By inflating certain inflatable members 142 to depress their associated dome regions 146 on the cassette 112, certain fluid flow passageways within the cassette 112 can be occluded. Thus, PD solution can be pumped through the cassette 112 by actuating the piston heads 134A, 134B, and can be guided along desired flow passageways within the cassette 112 by selectively inflating and deflating the inflatable members 142.

Figure 3:
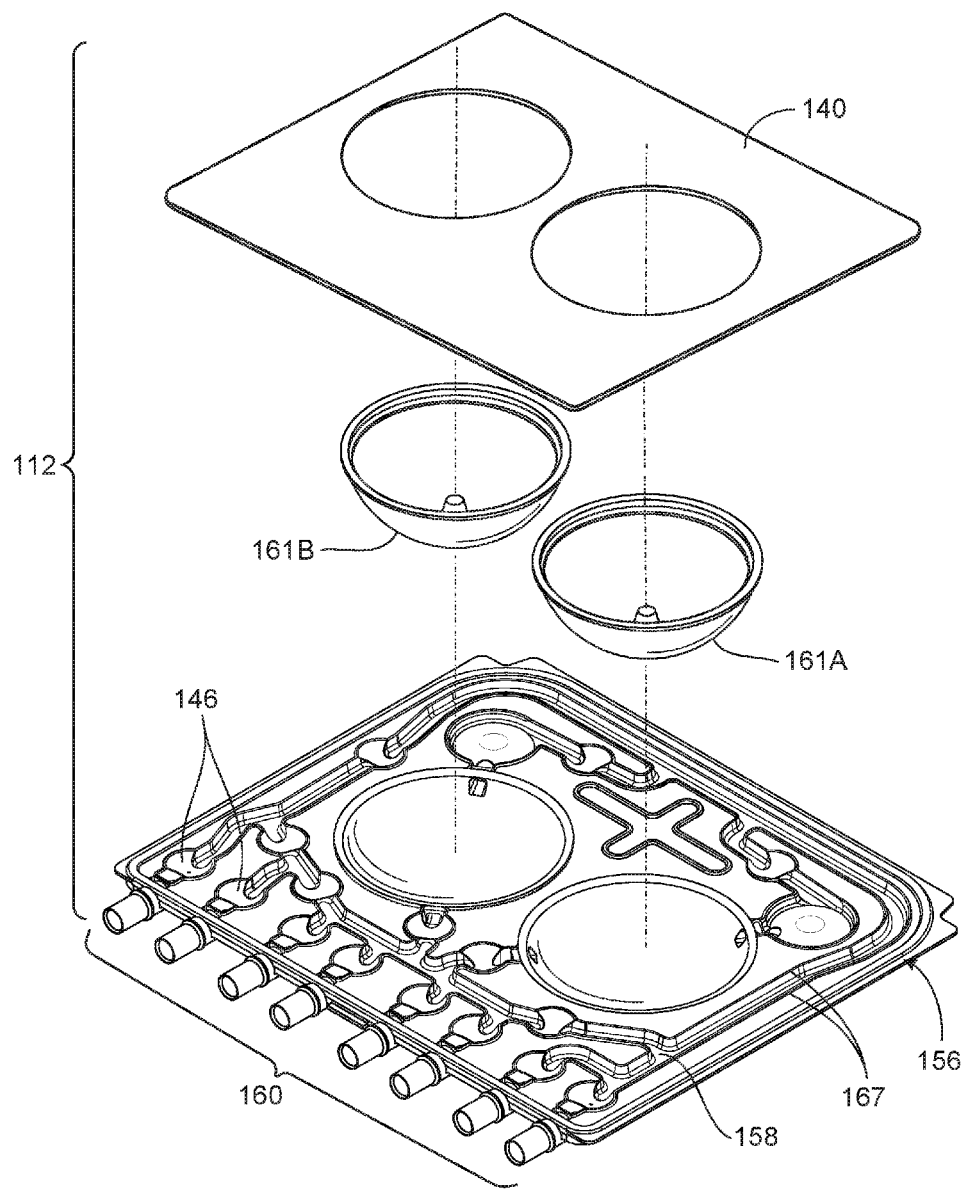
FIG. 3 is an exploded perspective view of the PD fluid cassette used with the PD cycler shown in FIG. 2.

Referring to FIG. 3, the PD fluid cassette 112 is a disposable unit that includes a flexible membrane 140 attached to a periphery of the tray-like rigid base 156. The base 156 includes raised ridges 167 that extend from the substantially planar surface of the base 156 towards and into contact with the inner surface of the flexible membrane 140 when the PD fluid cassette 112 is compressed between the door 108 and the cassette interface 110 of the PD cycler 102 to form a series of fluid passageways 158 and to form the multiple, depressible dome regions 146, which are widened portions (e.g., substantially circular widened portions) of the fluid passageways 158. The fluid passageways 158 fluidly connect the fluid line connectors 160 of the PD fluid cassette 112, which act as inlet/outlet ports of the PD fluid cassette 112, to the fluid pump chambers 138A, 138B. As noted above, the various inflatable members 142 of the PD cycler 102 act on the PD fluid cassette 112 during use. During use, the dialysis solution flows to and from the pump chambers 138A, 138B through the fluid passageways 158 and dome regions 146. At each depressible dome region 146, the membrane 140 can be deflected to contact the planar surface of the base 156 from which the raised ridges 167 extend. Such contact can substantially impede (e.g., prevent) the flow of dialysis solution along the region of the passageway 158 associated with that dome region 146. Thus, the flow of dialysis solution through the PD fluid cassette 112 can be controlled through the selective depression of the depressible dome regions 146 by selectively inflating the inflatable members 142 of the PD cycler 102.

Fluid line connectors 160 are positioned along the bottom edge of the cassette 112. As noted above, the fluid passageways 158 in the cassette 112 lead from the pumping chambers 138A, 138B to the various connectors 160. The connectors 160 are configured to receive fittings on the ends of the dialysis solution bag lines 126, the heater bag line 128, the patient line 130, and the drain line 132. One end of the fitting can be inserted into and bonded to its respective line and the other end can be inserted into and bonded to its associated connector 160. By permitting the dialysis solution bag lines 126, the heater bag line 128, the patient line 130, and the drain line 132 to be connected to the PD fluid cassette 112, as shown in FIGS. 1 and 2, the connectors 160 allow dialysis solution to flow into and out of the PD fluid cassette 112 during use.

Figure 4:
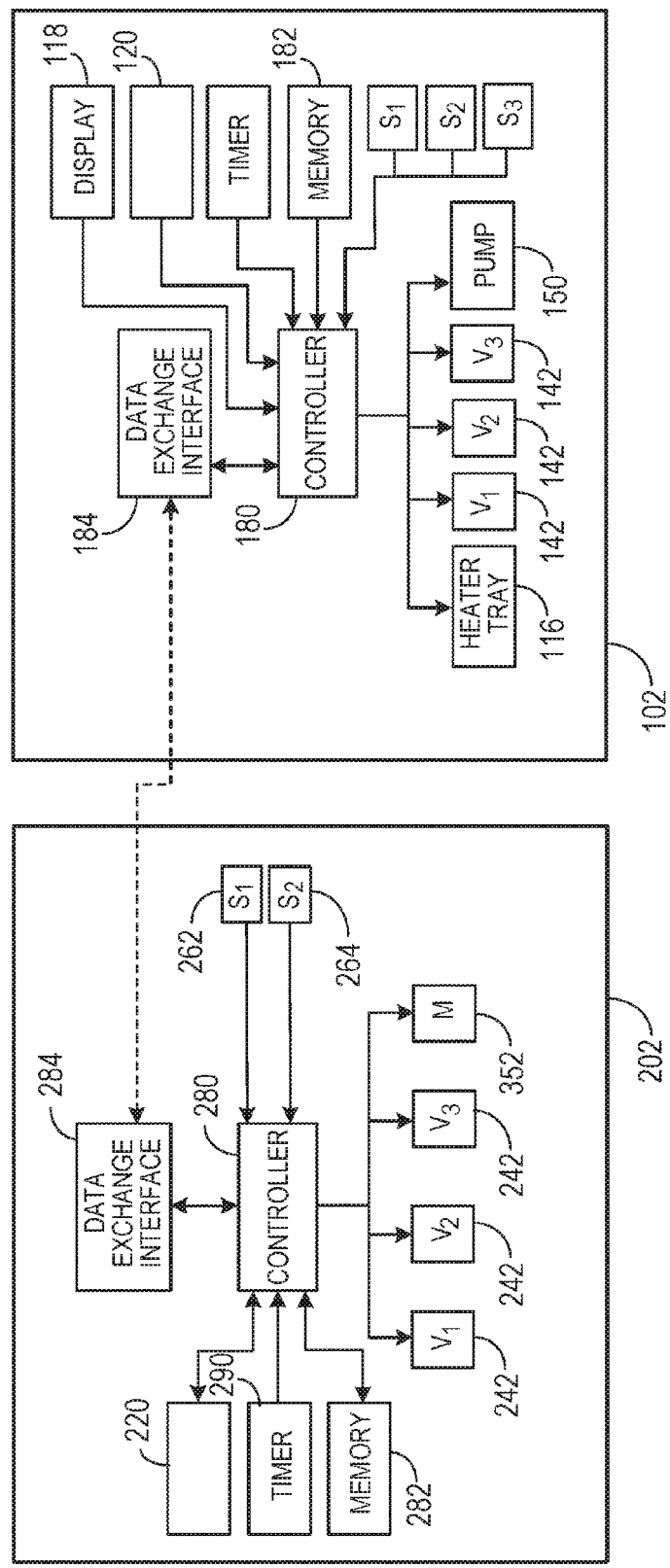
FIG. 4 is a schematic diagram illustrating control and communication systems within the PD system of FIG. 1.

Referring to FIG. 4, when the base PD system 101 is in use, the PD fluid cassette 112 is disposed within the compartment 114 of the PD cycler 102. The PC cycler 102 includes a controller 180 that controls the fluid pump 150 and inflatable members 142 to automatically deliver dialysate to and drain dialysate from a peritoneal cavity of a patient via the patient line 130. In particular, operation of the PD cycler 102 is controlled based on a patient treatment plan previously stored in a memory 182 in the PD cycler 102 and executed by the controller 180. The controller 180 is operable to permit transfer of information (for example, instructions for implementing dialysis treatment, patient treatment data, etc.) between the memory 182 and various information inputs or outputs, including, but not limited to, the touch screen 118, the control buttons 120, and a data transfer interface 184. The memory 182 can be any form of recordable medium such as a hard disk, a flash memory, RAM or other data storage device. In some embodiments, the memory 182 is non-volatile whereby it retains stored values when the external power is turned off. The controller 180 is configured to automatically modify the pre-stored patient treatment plan based on new instructions or data that has been input by the patient via the touch screen 118 and/or the control buttons 120, or based on patient treatment data received from the PD fluid exchange system 201 via the data transfer interface 184, as discussed further below.

Figure 5:
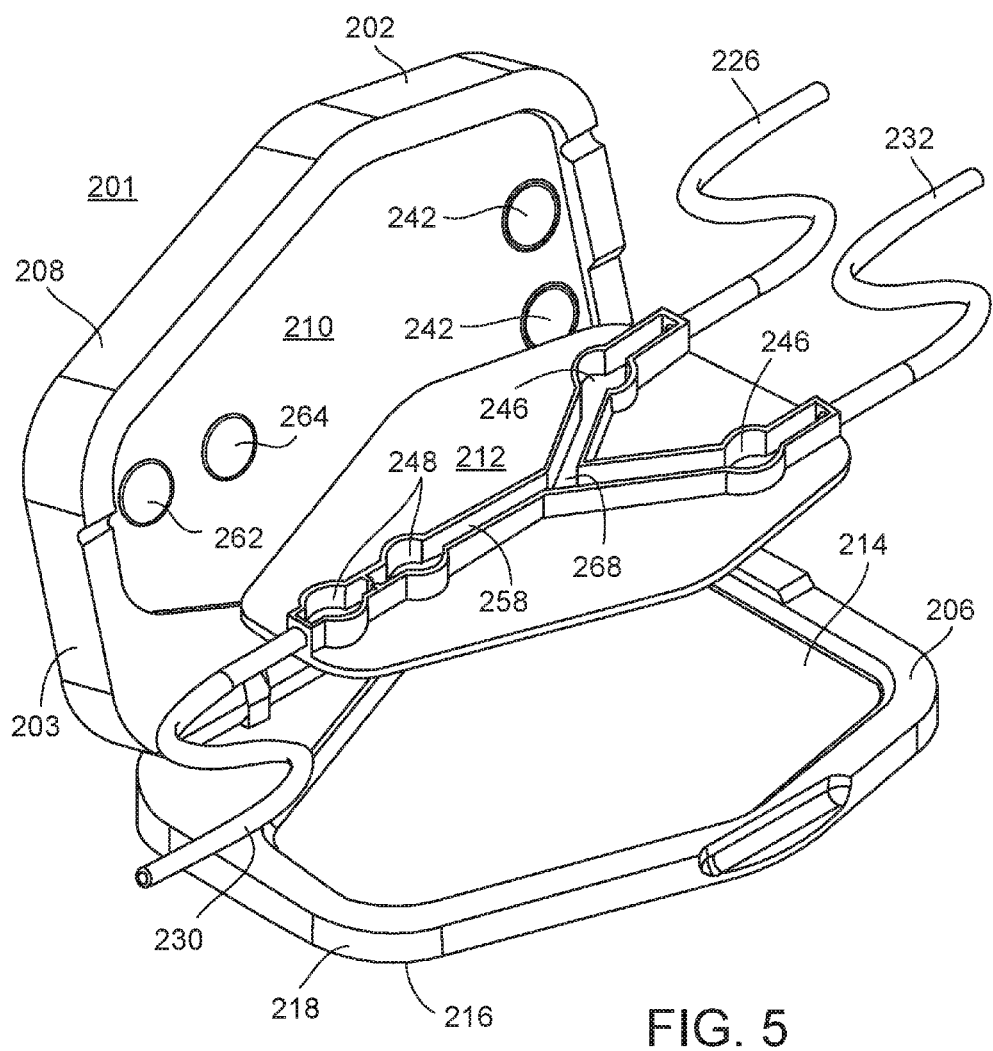
FIG. 5 is an exploded perspective view of a gravity-fed PD fluid exchange system.
Figure 6:
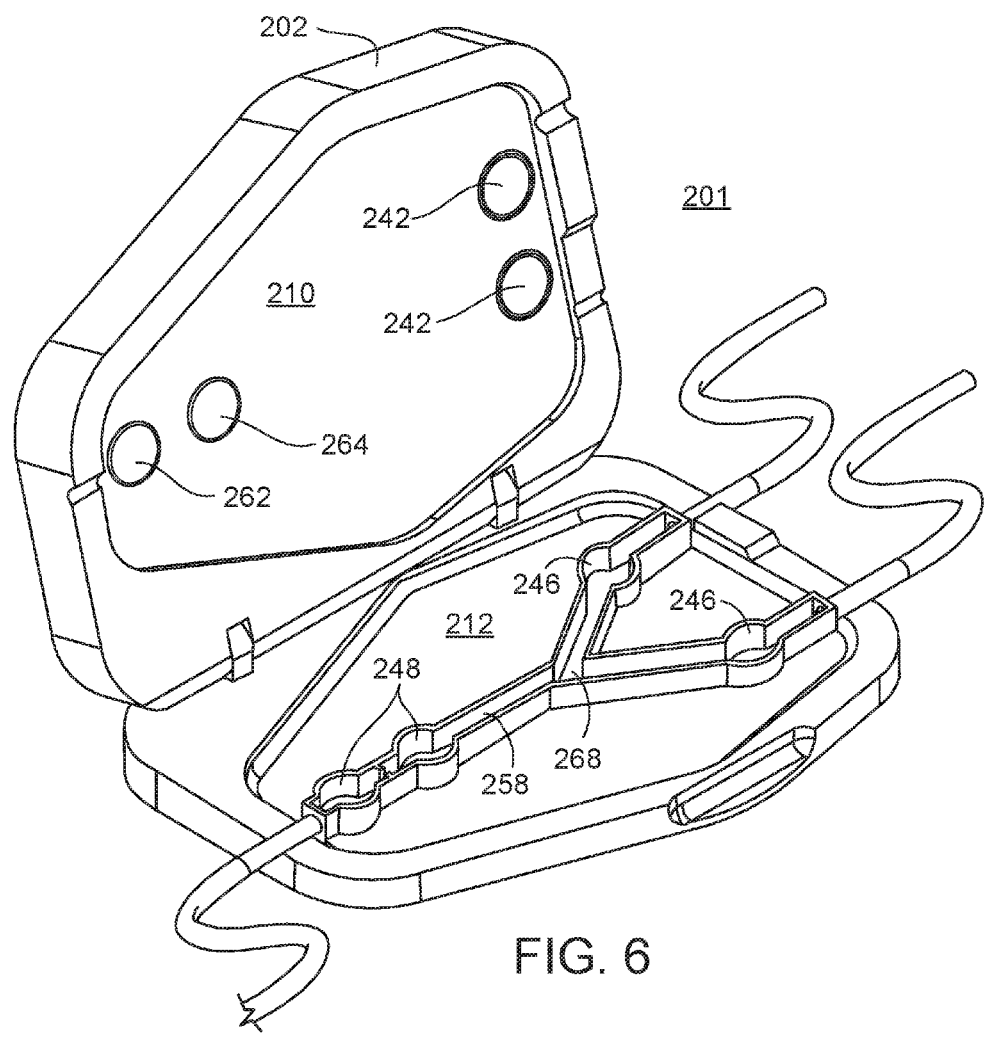
FIG. 6 is a perspective view of the PD fluid exchange system of FIG. 5 illustrating the PD fluid exchange cassette disposed within an open PD fluid exchange device.
Figure 7:
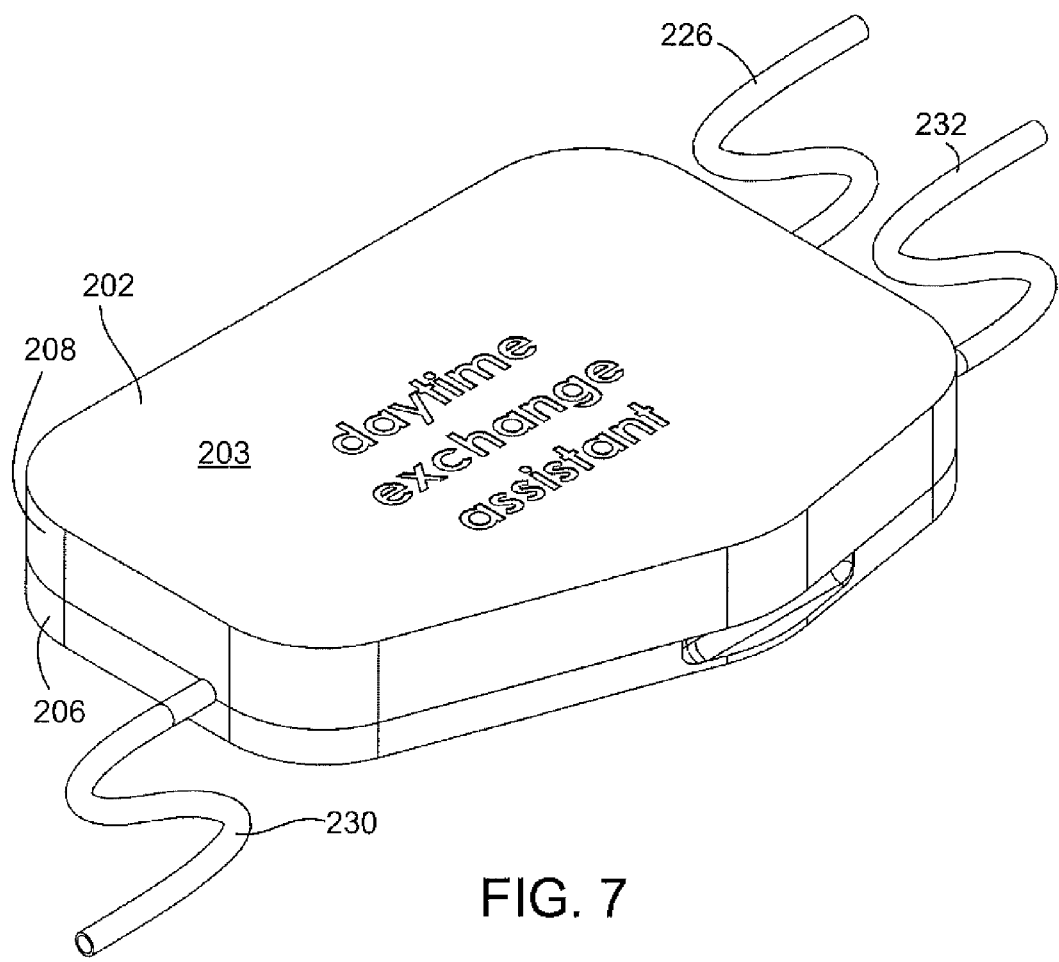
FIG. 7 is a perspective view of the PD fluid exchange system of FIG. 5 illustrating the PD fluid exchange cassette disposed within the closed PD fluid exchange device.

Referring to FIGS. 5-7, the PD fluid exchange system 201 includes the PD fluid exchange device 202 and the fluid exchange cassette 212. The PD fluid exchange device is small and sufficiently light in weight to be easily held in a single hand. For example, in some embodiments, the PD fluid exchange system 201 has a weight that is less than one lb prior to loading with fluid. As discussed further below, it contains valves, sensors and communications device that allow it to conduct a daytime fluid exchange, and communicate data obtained during the exchange to the patient's home-based PD cycler 102.

The PD fluid exchange device 202 includes a housing 203 that is thin relative to its length and width. The housing 203 has a "clam-shell" construction that includes a base 206 and a cover (door) 208 rotatably connected to the base 206. The base 206 includes a bottom 216 and sidewall 218 that extends around a periphery of the bottom 216 in a direction normal to the bottom 216. The bottom 216 and sidewall 218 together define a compartment 214. The door 208 is hinged to the sidewall 218 along one side of the housing 203, and is dimensioned and shaped to close the compartment 214. The door 208 includes a latch (not shown) that permits the door 208 to be selectively retained in the closed configuration shown in FIG. 7. In some embodiments, the latch is a magnetic latch.

The interior surface of the door 208 provides a cassette interface 210 that abuts the disposable fluid exchange cassette 212 when the fluid exchange cassette 212 is disposed within a cassette compartment 214 formed within the housing 203. The PD fluid exchange device 202 includes rigid valve members 242 positioned within valve ports in the cassette interface 210. The valve members are electrically controlled. For example, the valve member 242 may serve as an armature in a solenoid (not shown). Depending on the electrical state, the solenoid is used to advance the valve member 242 out of, or retract the valve member into, its respective valve port. The valve members 242 align with depressible valve seat dome regions 246 of the fluid exchange cassette 212 when the fluid exchange cassette 212 is positioned within the cassette compartment 214 of the PD fluid exchange device 202. The PD fluid exchange device 202 includes a valve member 242 associated with each of the valve seat dome regions 246 of the fluid exchange cassette 212. For example, in the embodiment illustrated in FIGS. 5 and 6, the PD fluid exchange device 202 includes two valve members 242 arranged to engage corresponding valve seat dome regions 246 of the fluid exchange cassette 212.

The valve members 242 direct dialysis solution through the fluid exchange cassette 212 in a desired manner during use. In particular, the valve members 242 protrude outward beyond the surface of the cassette interface 210 and into contact with the depressible valve seat dome regions 246 of the fluid exchange cassette 212 when actuate, and retract into the valve member ports and out of contact with the fluid exchange cassette 212 when deflated. By actuating certain valve members 242 to depress their associated valve seat dome regions 246 on the cassette 212, certain fluid flow passageways within the cassette 212 can be occluded. Thus, PD solution can be guided along desired flow passageways within the fluid exchange cassette 212 by selectively advancing and retracting the valve members 242.

The cassette interface 210 also supports a first pressure sensor 262 and a second pressure sensor 264. The first and second pressure sensors 262, 264 align with and directly contact sensor seat dome regions 248 of the fluid exchange cassette 212 when the fluid exchange cassette 212 is positioned within the cassette compartment 214 of the PD fluid exchange device 202. This arrangement allows detection of the fluid pressure within passageways 258 of the fluid exchange cassette 212.

Referring again to FIG. 4, the PD fluid exchange device 202 includes control buttons 220 that can be operated by a user (e.g., a patient) to allow, for example, set-up, initiation, and/or termination of a fluid exchange. In addition, the PD fluid exchange device 202 may be battery powered, or powered via wired connection to utility power. Although use of battery power allows for greater mobility, the use of utility power allows for a device having a relatively lower weight and cost as compared to a battery powered device.

A controller 280 is provided in the PD fluid exchange device 202 that receives data from the first and second pressure sensors 262, 264 corresponding to detected fluid pressures, and stores the received data on a storage medium (memory) 282 housed within the device 202. The controller 280 is configured to calculate fluid flow rates through the fluid passageway 258 based on the detected pressures and the known orifice diameter, and to also calculate the flow volumes based on the calculated fluid flow rate and the duration of flow through the restriction during an infusion procedure or a drain procedure. The calculated values are stored on the storage medium. For example, for each infusion procedure or drain procedure, the storage medium 282 stores at least the calculated fluid flow rates, the calculated duration of fluid flow, and the volume of fluid transferred to or from the patient.

The PD fluid exchange device 202 also includes a data transfer interface 284, and the controller 280 is configured to transfer the stored patient information data to the base PD cycler 102 via the data exchange interface 284, where the stored patient information data may include one or more of detected pressures, flow durations during an infusion procedure and/or a drain procedure, calculated flow fluid flow rates and calculated fluid volumes. In some embodiments, the data transfer interface 284 communicates with the PD cycler 102 wirelessly. For example, the data transfer interface 284 can use wireless standards and/or technologies such as Bluetooth®, secure wi-fi, and cellular networks to communicate with the PD cycler data transfer interface 184. Timing of the data transfer will depend on the communication range of the wireless communication technology used. For example, if the wireless communication technology has long range capabilities, data transfer from the PD fluid exchange device 202 to the PD cycler 102 may occur at the time the data is obtained and/or immediately following completion of a daytime fluid exchange. If the wireless communication technology has only short range capabilities, data transfer from the PD fluid exchange device 202 to the PD cycler 102 can occur when the PD fluid exchange device 202 is brought within the specified range. In other embodiments, the data transfer interface 284 communicates with the PD cycler 102 using a wired connection such as a universal serial bus (USB), serial cable, or other direct connection.

Referring to FIGS. 8 and 9, the fluid exchange cassette 212 is a disposable unit that includes a flexible membrane 240 (not shown in FIG. 8) attached to a periphery of a tray-like rigid base 256. The base 256 includes raised ridges 267 that extend from the substantially planar surface of the base 256 towards and into contact with the inner surface of the flexible membrane 240 when the fluid exchange cassette 212 is compressed between the door 208 and the cassette interface 210 of the fluid exchange device 202 to form a series of fluid passageways 258. In the fluid exchange cassette 212, the fluid passageways 258 are in the form of a "Y" including a patient line portion 258a that has a bifurcation 268 at which the patient line portion 258a converts to a fluid supply line portion 258b and a fluid drain line portion 258c. The fluid passageways 258a, 258b, 258c fluidly connect to the fluid line connectors 260 of the fluid exchange cassette 212, which act as inlet/outlet ports of the fluid exchange cassette 212.

The ridges 267 also form two, depressible valve seat dome regions 246 and two sensor seat dome regions 248 which are widened portions (e.g., substantially circular widened portions) of the fluid passageways 258. The valve seat dome regions 246 serve as valve seats within the fluid passageways 258. A valve seat dome region 246 is provided in each of the fluid supply line portion 258b and the fluid drain line portion 258c, and is located between the bifurcation 268 and the corresponding fluid line connector 260.

Referring also again to FIG. 5, a patient line 230 is connected to the patient line portion 258a via a fluid connector 260 at one end 252 of the fluid exchange cassette 212. At the opposed end 254 of the fluid exchange cassette 212, a dialysis solution bag line 226 is connected to the fluid supply line portion 258b via a fluid connector 260 and a drain line 232 is connected to the fluid drain line portion 258c via a fluid connector 260. The patient line 230 can be connected to a patient's abdomen via a catheter and can be used to pass dialysis solution back and forth between the fluid exchange cassette 212 and the patient during use. The dialysis solution bag line 226 can be connected to a dialysis solution bag, and can be used to pass dialysis solution from the dialysis solution bag to the fluid exchange cassette 212 during use. The drain line 232 can be connected to a drain or drain receptacle and can be used to pass dialysis solution from the fluid exchange cassette 212 to the drain or drain receptacle during use.

The fluid exchange cassette 212 is a "gravity feed" cassette since fluid flow through the fluid exchange cassette 212 occurs under force of gravity, while the dialysis solution bag is placed higher than the patient, and the drain or drain receptacle is placed lower than the patient.

As noted above, when the fluid exchange cassette 212 is disposed within the PD fluid exchange device 202, the valve members 242 of the PD fluid exchange device 202 act on the fluid exchange cassette 212 during use. During use, the dialysis solution flows through the fluid passageways 258 and dome regions 246, 248. At each valve seat dome region 246, the membrane 240 can be deflected to contact the planar surface of the base 256 from which the raised ridges 267 extend. Such contact can substantially impede (e.g., prevent) the flow of dialysis solution along the region of the passageway 258 associated with that valve seat dome region 246. Thus, the flow of dialysis solution through the fluid exchange cassette 212 can be controlled through the selective depression of the valve seat dome regions 246 by selectively actuating the valve members 242 of the PD fluid exchange device 202.

The sensor seat dome regions 248 serve as sensor seats within the fluid passageways 258. Both sensor seat dome regions 248 are located in the patient line portion 258a, between the bifurcation and the corresponding fluid line connector 260. The ridges 267 also form a localized region of reduced fluid passageway diameter (e.g., reduced-diameter region) 270. In some embodiments, the ridges 267 form an orifice plate at this location, including an orifice 272 having a predetermined diameter that is less than the diameter of the passageway 258a adjoining the orifice plate on each side of the orifice plate. The reduced-diameter region 270 is disposed in the patient line portion 258a between the sensor seat dome regions 248.

When the fluid exchange cassette 212 is disposed within the PD fluid exchange device 202, a pressure sensor 262, 264 is positioned at each of the sensor seat dome regions 248. The pressure sensors 262, 264 detect fluid pressure within the passageway 258 external to the fluid flow. In particular, the pressure sensors 262, 264 contact the flexible membrane 240, and thus do not directly contact the fluid flowing within the passageway 258 during pressure detection. In addition, the arrangement of pressure sensors 262, 264 in the sensor seat dome regions 248 located on either side of the reduced-diameter region 270 permits measurement of fluid pressures within the passageway 258 on each side of the reduced-diameter region 270. The measured pressures, along with the known dimension of the orifice 272, allow for the measurement of the fluid flow rate in the patient line portion 258a, which corresponds to the fluid flow rate into and out of the patient during a fluid exchange. Thus, the fluid exchange cassette 212 and the PD fluid exchange device 202 cooperate to form a flow meter within the PD fluid exchange system 201. The pressure-based method of fluid flow rate measurement used in the PD fluid exchange system 201 also allows for dynamic flow rate monitoring (e.g., measurement of the fluid flow rate as it changes, depending on conditions), yielding accurate flow rate measurements. Moreover, measuring the fluid flow rate into and out of the patient as well as the duration of fluid flow allows for calculation of the fluid volume infused and drained during a fluid exchange.

Figure 10:
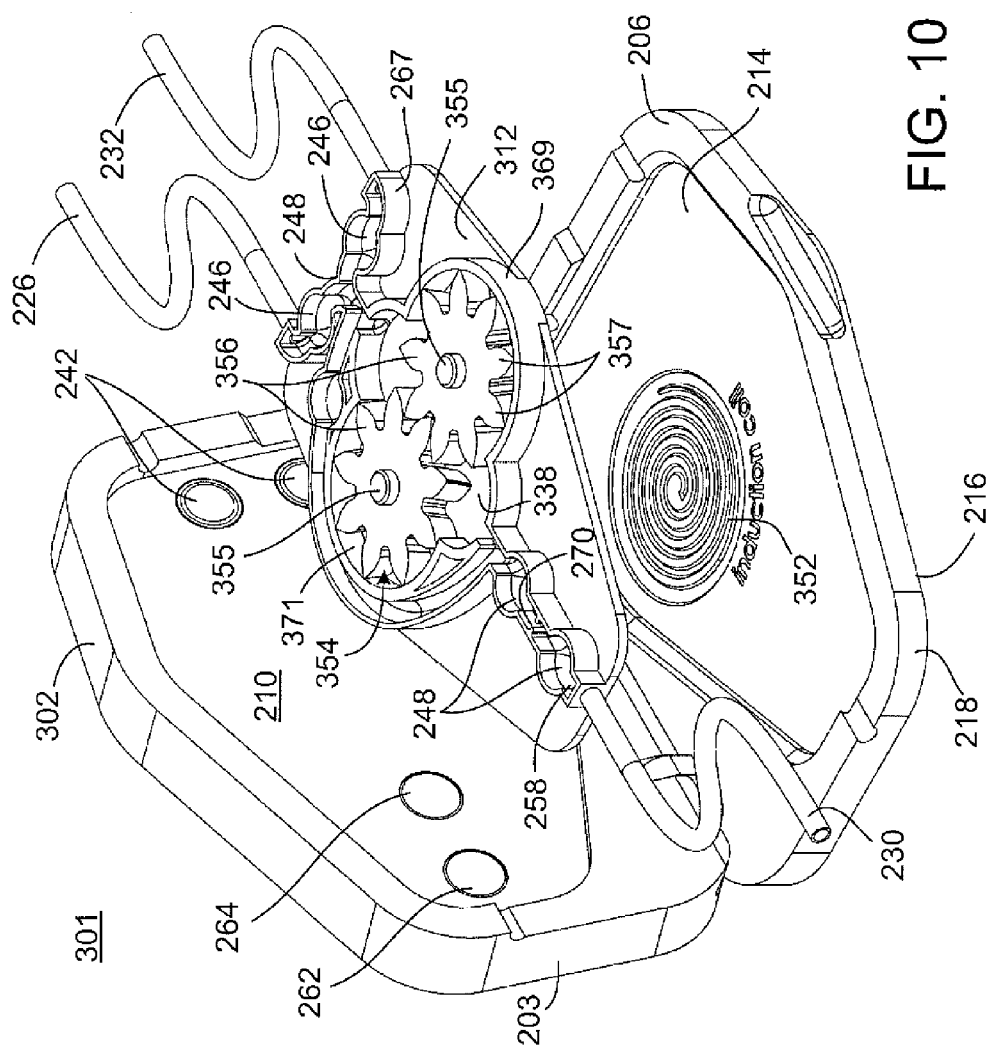
FIG. 10 is an exploded perspective view of a pump-fed PD fluid exchange system.

Referring to FIG. 10, another PD fluid exchange system 301 includes a PD fluid exchange device 302 and a fluid exchange cassette 312. As in the previous embodiment, the PD fluid exchange device 302 is small and sufficiently light in weight to be easily held in a single hand. In addition to containing the valves, sensors and communications device described in the previous embodiment, the PD fluid exchange system 301 also includes integrated fluid pumping, as discussed below.

The fluid exchange cassette 312 is similar to the fluid exchange cassette 212 and in the following description, like parts have common reference numbers and will not be described again. In addition to the features of the fluid exchange cassette 212, the fluid exchange cassette 312 also includes a pump chamber 338 disposed in the fluid passageway 258 between the reduced diameter region 270 and the bifurcation 268, and a rotor assembly 354 that resides in the pump chamber 338. In particular, the raised ridges 267 that form the passageway 258 have a widened portion 369 that forms the pump chamber 338. In the illustrated embodiment, the pump chamber 338 is much larger than the depressible dome regions 246. The rotor assembly 354 may include a pair of rotors 356 including rotor teeth 357, and the rotors 356 are arranged so that the rotor teeth 357 are tightly meshed, whereby fluid is driven through the pump chamber 338 about an outer periphery of the rotor teeth 357 along an inner surface 371 of the widened portion 369. In addition, the widened portion 369 has a peripheral shape and dimension that is fitted to a periphery of the rotor assembly 354. As a result of the arrangement in which the rotor teeth are tightly meshed and the pump chamber is fitted to a periphery of the rotor assembly, fluid flow through the pump chamber 338 occurs only when the rotor assembly 354 is actuated.

The PD fluid exchange device 302 is similar to the PD fluid exchange device 202 and in the following description, like parts have common reference numbers and will not be described again. In addition to the features of the PD fluid exchange device 202, the PD fluid exchange device 302 also includes an actuator 352 disposed in a vacancy formed in the housing bottom 216. The actuator 352 engages the rotor assembly 354 disposed within the pump chamber 338 provided in the PD fluid exchange cassette 312 so that the rotors 356 rotate about pins 355. The actuator 352, together with the rotor assembly 354 and pump chamber 338, forms a fluid pump 350 for pumping fluid through the PD fluid exchange cassette 312. In the illustrated embodiment, the fluid pump is an induction driven magnetic pump, and the actuator 352 is an induction coil that generates a rotating magnetic field used to drive the rotor assembly 354. In addition, the controller 280 is configured to control the direction and speed of the rotors 356 via the actuator 352.

Since the PD fluid exchange system 301 includes the integrated pumping system, it can pump fluid against gravity, removing the need to manually raise the dialysis solution bag and manually lower the drain relative to the patient. In addition, the rate of fluid exchange can be controlled, and in some cases may result in a faster fluid exchange than when performed using a gravity feed.

Figure 11:
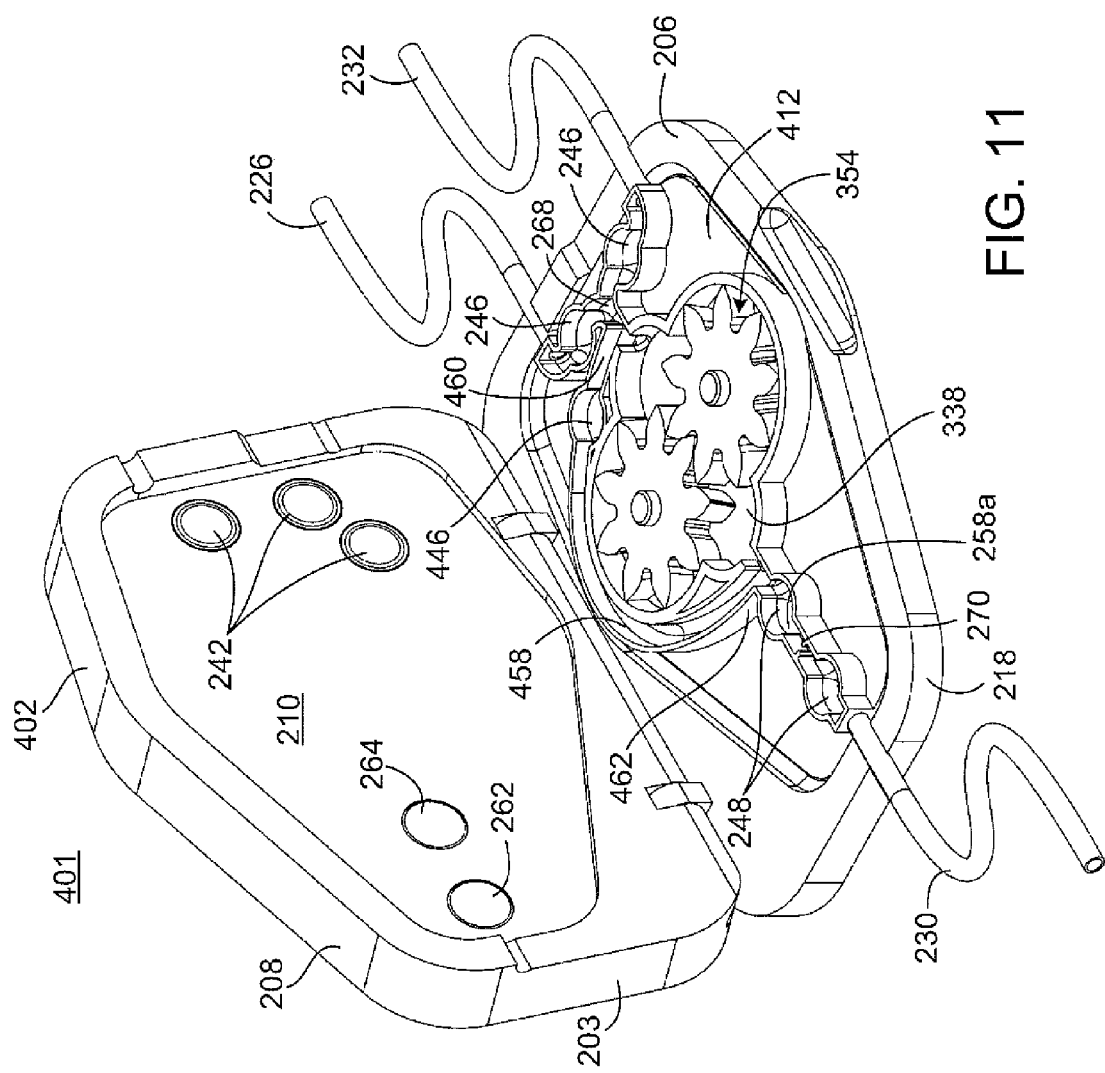
FIG. 11 is an exploded perspective view of a PD fluid exchange system that can be either gravity-fed or pump-fed.

Referring to FIG. 11, another PD fluid exchange system 401 includes a PD fluid exchange device 402 and a fluid exchange cassette 412. As in the previous embodiment, the PD fluid exchange device 402 is small and sufficiently light in weight to be easily held in a single hand, and contains pumping, valves, sensors and communications device described in the previous embodiment. In addition, the PD fluid exchange system 401 also includes a bypass passageway 458 to permit selection between gravity feed fluid exchange and pump feed fluid exchange, as discussed below.

The PD fluid exchange device 402 is similar to the PD fluid exchange device 302 and in the following description, like parts have common reference numbers and will not be described again. In addition to the features of the PD fluid exchange device 302, the PD fluid exchange device 402 also includes an additional valve member 242 positioned within a corresponding valve member port in the cassette interface 210. The additional valve member 442 is aligned with a depressible valve seat dome region 446 of the bypass passageway 458 when the fluid exchange cassette 412 is positioned within the cassette compartment 214 of the PD fluid exchange device 402. As in previous embodiments, the PD fluid exchange device 402 includes a valve member 242 associated with each of the valve seat dome regions 246 of the fluid exchange cassette 412. For example, in the embodiment illustrated in FIG. 11, the PD fluid exchange device 402 includes three valve members 242 arranged to engage corresponding valve seat dome regions 246, 446 of the fluid exchange cassette 412 and act as valves to direct dialysis solution through the fluid exchange cassette 412 in a desired manner during use. By actuating (e.g. advancing) the third valve member 242 to depress it's associated valve seat dome region 446 on the fluid exchange cassette 412, the bypass fluid passageway 458 within the fluid exchange cassette 412 can be occluded. When the third valve member 242 is actuated so as to close the bypass fluid passageway 458, the flow of PD solution through the fluid exchange cassette 412 can be controlled by controlling the fluid pump 350. For example, when the fluid passageway 458 is closed, operation of the actuator 352 causes fluid to flow through the pump chamber 338, and stopping the actuator 352 causes fluid flow through the fluid exchange cassette 412 to stop. Alternatively, when the third valve member 242 is retracted so as to open the bypass fluid passageway 458 and the actuator 352 is stopped, the PD solution may be gravity fed through the fluid exchange cassette 412 via the bypass fluid passageway 458.

The fluid exchange cassette 412 is similar to the fluid exchange cassette 312, and in the following description, like parts have common reference numbers and will not be described again. In addition to the features of the fluid exchange cassette 312, the fluid exchange cassette 412 also includes the bypass passageway portion 458 that selectively permits fluid flow to be diverted past the pump chamber 338. To this end, the bypass fluid passageway 458 has a first end 460 that intersects and fluidly communicates with the patient line portion 258a at a location between the pump chamber 338 and the bifurcation 268, and a second end 462 that intersects and fluidly communicates with the patient line portion 258a at a location between the pump chamber 338 and the adjacent pressure sensor seat 248. In addition, the bypass fluid passageway 458 includes the bypass valve seat 446 that is configured to receive the valve member, as previously discussed.

Since the fluid exchange cassette 412 includes the bypass fluid passageway 458 having the bypass valve seat 446, the PD fluid exchange system 401 can provide a daytime fluid exchange that can be either a gravity feed exchange or a pumping feed exchange.

A method of providing dialysis treatment using the medical fluid pumping system 100 having a base PD system 101 and a peritoneal dialysis fluid exchange system 201, 301, 401 will now be described.

CAPD is performed using the peritoneal fluid exchange system 201, 301, 401, and patient treatment data is obtained during the daytime fluid exchange. In particular, the controller 280 receives sensor data detected by fluid pressure sensors 262, 264 during infusion portions and drain portions of the daytime fluid exchange, and determines patient treatment data corresponding to the daytime fluid exchange. For example, based on the detected pressures upstream and downstream of the reduced diameter region 270 and the known size of the opening of the reduced diameter region 270, the controller 280 calculates the fluid flow rate within the patient line portion 258a of the cassette fluid passageways 258. Based on the duration of the fluid exchange as measured by a timer 290, the volume of fluid delivered and/or drained from the patient during the fluid exchange is also calculated. In some embodiments, the patient treatment data obtained by the PD fluid exchange device 202, 302, 402 may include, but is not limited to, the detected pressures during fluid exchange, the duration of fluid exchange, the calculated fluid flow rate during fluid exchange, the volume of fluid transferred to the patient during fluid exchange, the volume of fluid drained from the patient during fluid exchange, the time of the fluid exchange and the date of the fluid exchange. In some embodiments, the patient treatment data is stored in memory 282 of the PD fluid exchange device 202, 302, 402.

The obtained patient treatment data is transferred from the data exchange interface 284 of the peritoneal fluid exchange device 202, 302, 402 to the data exchange interface 184 of the PD cycler 102. In some embodiments, the obtained patient treatment data is transferred from the memory 282 of the PD fluid exchange device 202, 302, 402 to the PD cycler 102 after a time delay. In other embodiments, the obtained patient treatment data is transferred to the PD cycler 102 of the base PD system 101 concurrent with its storage in memory 282 of the PD fluid exchange device 202, 302, 402. In still other embodiments, the obtained patient treatment data is transferred to the PD cycler 102 of the base PD system 101 without storage in the memory 282 of the PD fluid exchange device 202, 302, 402. As previously discussed, the data transfer may be achieved wirelessly or through a direct-wired connection between the data exchange interface 284 of the PD fluid exchange device 202, 302, 402 and the data exchange interface 184 of the PD cycler 102.

The transferred patient treatment data is received by the data exchange interface 184 of the PD cycler 102 and stored in the memory 182 of the PD cycler 102. The controller 180 of the PD cycler 102 receives the transferred patient data from the data exchange interface 184 or reads the transferred patient data from the memory 182. In some embodiments, the transferred patient treatment data is synchronized with previously-stored patient treatment data of the PD cycler 102 including patient treatment data obtained during CCPD using the PD cycler 102. The transferred patient treatment data may also be synchronized with a previously-stored patient treatment plan. As used herein, the term "synchronized" refers to causing the transferred patient treatment data to be inserted into the PD cycler memory 182 and combined with previously stored patient treatment data and other information such that a time ordering of all the patient treatment data is obtained. The PD cycler controller 180 then determines a modified patient treatment plan using the base peritoneal dialysis system 101 based on, at least in part, the obtained patient treatment data transferred from the PD fluid exchange system 201, 301, 401.

In some instances, in view of the volume of fluid infused to the patient, the volume of fluid drained from the patient and/or the duration fluid exchange during the daytime fluid exchange using the peritoneal fluid exchange device 202, 302, 402, the PD cycler controller 180 may determine that an insufficient fluid exchange was performed during the daytime fluid exchange. In this case, the PD cycler controller 180 may then modify the patient treatment plan to be performed by the PD cycler 102 during the next CCPD to correct for the insufficiency, for example by increasing fluid exchange during the next CCPD. To correct for an insufficiency, the PD cycler controller 180 may increase an infusing volume, increase an infusing duration, reduce a draining volume, reduce a draining duration, or a combination of these. The user may also be alerted by the machine if an insufficient fluid exchange was performed during the daytime fluid exchange.

In other instances, in view of the volume of fluid infused to the patient, a volume of fluid drained from the patient and/or the duration fluid exchange during the daytime fluid exchange using the peritoneal fluid exchange device 202, 302, 402, the PD cycler controller 180 may determine that an excessive fluid exchange was performed during the daytime fluid exchange. In this case, the PD cycler controller 180 may then modify the patient treatment plan to be performed by the PD cycler 102 during the next CCPD to correct for the excess, for example by decreasing the amount of fluid exchanged during the next CCPD. To correct for an excess, the PD cycler controller 180 may decrease an infusing volume, decrease an infusing duration, increase a draining volume, increase a draining duration, or a combination of these. The user may also be alerted by the machine if an excessive fluid exchange was performed during the daytime fluid exchange.

In still other instances, in view of the volume of fluid infused to the patient, a volume of fluid drained from the patient and/or the duration fluid exchange during the daytime fluid exchange using the peritoneal fluid exchange device 202, 302, 402, the PD cycler controller 180 may determine that adequate fluid exchange was performed during the daytime fluid exchange, and no modifications may be made to the patient treatment plan to be performed by the PD cycler 102 during the next CCPD.

In still other instances, in view of the volume of fluid infused to the patient, a volume of fluid drained from the patient and/or the duration fluid exchange during the daytime fluid exchange using the peritoneal fluid exchange device 202, 302, 402, the PD cycler controller 180 may determine that insufficient fluid was drained from the patient during the daytime exchange. In this case, the PD cycler controller 180 may then modify the patient treatment plan to be performed by the PD cycler 102 during the next CCPD to correct for the insufficient fluid drain, for example by decreasing the amount of fluid infused during first cycle of the next CCPD, or by adding a draining step prior to the first cycle of the next CCPD.

CCPD may then be performed using the PD cycler 102 in accordance with the patient treatment plan including any modifications made to the plan by the PD cycler controller 180.

The PD cycler 102 is described herein as being operable to permit transfer of information (for example, instructions for implementing dialysis treatment, patient treatment data, etc.) between the memory 182 and various information inputs or outputs, including the data transfer interface 184. Although transfer of information from the PD fluid exchange device 202, 302, 402 to the PD cycler is discussed, information can also be transferred from the PD cycler 102 to the PD fluid exchange device 202, 302, 402. For example, in embodiments in which there is an active pumping mechanism, the PD cycler 102 can communicate preset parameters including, but not limited to, flow rate, pressure, fill volume, and drain volume to the PD fluid exchange device 202, 302, 402. Advantageously, this feature minimizes a need for the patient to input data to the PD fluid exchange device 202, 302, 402, since using the PD fluid exchange device 202, 302, 402 having transferred information would merely require inserting the fluid exchange cassette into the PD fluid exchange device, connecting the fluid bags and catheter line, and turning on the PD fluid exchange device 202, 302, 402. In some implementations, all of the exchange parameters can be preprogrammed by the PD cycler 102, which would communicate the exchange parameters to the PD fluid exchange device 202, 302, 402. As a result, the PD fluid exchange device 202, 302, 402 can conduct the desired fill, dwell, and drain sequence automatically with no patient interaction.

The fluid pump of the fluid exchange device 302, 402 is described herein as an induction driven magnetic pump, and the actuator 352 is an induction coil that generates a rotating magnetic field used to drive the rotor assembly 354 that is located within the fluid passageway 258. This type of fluid pump, where the rotor assembly 354 is disposed within the fluid passageway 258, is advantageous because the induction type drive system is small and light-weight, contributing to the small size and portability of the fluid exchange device 302, 402. However, the fluid pump is not limited to an induction driven magnetic pump. For example, fluid pumping can be achieved using a pumping system such as the fluid pump 150 used in the PD cycler 102, or peristaltic pump, in which the pumping mechanisms are external to the fluid passageway 258.

While the PD fluid exchange devices have been described as including rigid valve members 242 that advance outward from and retract into valve ports in the cassette interface 210, the PD fluid exchange devices are not limited to using rigid valve members to selectively occlude fluid flow in cassette fluid passageways. In one example, other mechanical devices such as actuatable clamps or rods may be provided on the cassette interface to selectively occlude fluid flow in cassette fluid passageways. In another example, the valve members may be inflatable members positioned within inflatable member ports in the cassette interface 210. In addition, while rigid valve members 242 are described herein as being electrically-controlled, the valve members 242 may be actuated using other methods. For example, in some embodiments, the valve members may be pneumatically or hydraulically controlled.

While the PD cycler 102 includes pistons 133A, 133B that can be mechanically connected to dome shaped fastening members 161A, 161B of the cassette 112 overlying the pump chambers 138A, 138B, and the motors, pistons 133A, 133B, and piston heads 134A, 134B serve as the fluid pump 150 that, in cooperation with the pump chambers 138A, 138B, drives fluid through the PD cassette 112, the PD cycler 102 and PD cassette 112 are not limited to these configurations and the PD cycler can implement other fluid pumps and pumping systems. For example, the PD cycler 102 may include a vacuum system that cooperates with the pistons 133A, 133B and the cassette 112 to obtain volume changes within the cassette pump chambers 138A, 138B.

While the PD cycler 102 is described herein as being used with the PD cassette 112, the PD cycler 102 may be used with any of various other types of cassettes. For example, the PD fluid cassette the PD fluid cassettes can alternatively have more or fewer than two pump chambers. For another example, the PD fluid cassette may be formed of a rigid frame having a flexible membrane on each opposed side of the frame. Moreover, in some embodiments, the PD cycler may be of a type that does not use a cassette.

While the base PD system 101 including the PD cycler 102 and the PD cassette 112 are described as being designed for home use, it is understood that these devices can be used in other settings such as a clinic.

While the PD fluid exchange device 202 is described herein as being small and sufficiently light in weight to be easily held in a single hand, in some embodiments the PD fluid exchange device may not be easily held in a single hand, while still being more portable than the PD cycler.

While the PD fluid exchange device 202 is described herein as employing a pressure-based flow meter including the orifice plate 270 and corresponding sensors 262, 264 to measure the flow rate, the PD fluid exchange device is not limited to this flow rate measuring structure and may include other techniques and/or structures to measure the flow rate. In some embodiments, other flow restricting structures such as a venturi nozzle may be disposed between the pressure sensors 262, 264. In other embodiments, mechanical or optical flow meters may be employed to measure flow rate in the fluid passageways. In still other embodiments, the flow meter may be omitted, and fluid flow may be measured indirectly, for example by tracking the rotation of the rotors 356 and calculating a flow rate based on a known volume displaced by movement of the rotors 356 within the pump chamber 338.

The PD fluid exchange cassettes are described herein as including a flexible membrane 240 attached to a periphery of the rigid base 256. In some embodiments, to compensate for the presence of the raised ridges that define the fluid passageways, the rigid base may be formed having a slightly raised outer rim (not shown), and the membrane 240 is then attached to the rim. The arrangement of attaching the membrane 240 around the peripheral edge of the rigid base 256 is advantageous because the periphery of the rigid base 256 is usually regular in shape, and thus is easier to seal. However, in some embodiments, the membrane 240 may be attached to the raised ridges that define the fluid passageways.

While the PD system 100 has been described herein as being used to perform peritoneal dialysis, the system can be used in other fluid-pumping applications including, but not limited to, hemodialysis. For example, the PD system 100 may be used in any application requiring a portable device that is capable of pumping fluid cleanly and accurately.

While many of the systems above have been described as being used to pump dialysis solution, other types of dialysis fluids can be pumped through the cassettes. As an example, in the case of cassettes used with hemodialysis machines, blood can be pumped through the cassettes. In addition, priming solutions, such as saline, can similarly be pumped through cassettes using the various different systems and techniques described above. Similarly, as an alternative to dialysis fluids, any of various other types of medical fluids can be pumped through the above-described cassettes depending on the type of medical fluid pumping machines with which the cassettes are used.

A number of embodiments have been described. Nevertheless, it will be understood that various modifications may be made without departing from the spirit and scope of the disclosure. Accordingly, other embodiments are within the scope of the following claims.

What is claimed is:

1. A peritoneal dialysis system comprising a base peritoneal dialysis system and a peritoneal dialysis fluid exchange system that operates independently of the base peritoneal dialysis system, wherein the base peritoneal dialysis system includes
a first disposable unit including a first patient line configured to be connected to a patient, and
a peritoneal dialysis device including
a compartment configured to receive the first disposable unit, and
at least one pump arranged so that when the first disposable unit is disposed within the compartment, the pump cooperates with the first disposable unit to deliver dialysate to and drain dialysate from a peritoneal cavity of the patient via the first patient line of the first disposable unit,
the peritoneal dialysis fluid exchange system has a size and a weight that are less than a size and a weight of the base peritoneal dialysis system, and the peritoneal dialysis fluid exchange system includes
a second disposable unit including
a second patient line configured to be connected to the patient such that fluid can be delivered to and drained from the peritoneal cavity of the patient via the second patient line, and
at least one valve seat,
a fluid exchange device that is sized to be handheld, the fluid exchange device including
a compartment configured to receive the second disposable unit,
at least one valve member arranged to cooperate with the at least one valve seat of the second disposable unit when the second disposable unit is disposed in the compartment, and
a data exchange interface operable to transfer patient treatment data from the peritoneal dialysis fluid exchange system to the base peritoneal dialysis system, and the base peritoneal dialysis system is configured to
automatically deliver dialysate to and automatically drain dialysate from the peritoneal cavity of the patient based on a patient treatment plan, and
modify the patient treatment plan based on the patient treatment data transferred from the peritoneal dialysis fluid exchange system.

2. The system of claim 1, wherein the data exchange interface is a transmitter, and the base peritoneal dialysis system further comprises a receiver.

3. The system of claim 1, wherein the data exchange interface is an input/output port configured to permit connection to a data communication line extending from the base peritoneal dialysis system.

4. The system of claim 1, wherein the peritoneal dialysis fluid exchange system comprises a fluid flow meter.

5. The system of claim 1, wherein the fluid exchange device further comprises a sensor disposed adjacent to the second disposable unit when the second disposable unit is disposed in the compartment of the fluid exchange device, the sensor being operable to obtain the patient treatment data.

6. The system of claim 1, wherein the patient treatment data includes a volume of fluid transferred to the patient and a volume of fluid drained from the patient.

7. The system of claim 1, wherein the peritoneal dialysis fluid exchange system includes a processor configured to
calculate fluid flow rates through the peritoneal dialysis fluid exchange system,
calculate a duration of fluid flow through the peritoneal dialysis fluid exchange system, and
use the calculated fluid flow rates and the calculated duration to determine at least one of a volume of fluid infused to the patient and a volume of fluid drained from the patient.

8. The system of claim 7, wherein the processor is further configured to store at least one of the calculated fluid flow rates, the calculated duration, the volume of fluid transferred to the patient and the volume of fluid drained from the patient.

9. The system of claim 7, wherein the second disposable unit comprises
a base, and
a flexible membrane attached to the base in such a way that the base and the flexible membrane cooperate to form a fluid passageway that can be placed in communication with the second patient line,
wherein
the fluid passageway includes a first pressure sensor seat, a second pressure sensor seat, and a localized region of reduced fluid passageway diameter disposed between the first pressure sensor seat and the second pressure sensor seat.

10. The system of claim 1, wherein the second disposable unit comprises
a base, and
a flexible membrane attached to the base in such a way that the base and the flexible membrane cooperate to form a fluid passageway that can be placed in communication with the second patient line, the second patient line having a patient line portion connected to an infusion line portion and a drain line portion,
wherein
the patient line portion includes a first pressure sensor seat, a second pressure sensor seat, and a localized region of reduced fluid passageway diameter disposed between the first pressure sensor seat and the second pressure sensor seat.

11. The system of claim 10, wherein
the fluid exchange device includes a first pressure sensor and a second pressure sensor,
the fluid exchange device is configured to receive the second disposable unit within the fluid exchange device compartment in a manner such that the first pressure sensor is disposed at a location corresponding to the first pressure sensor seat, and the second pressure sensor is disposed at a location corresponding to the second pressure sensor seat, and
the fluid exchange device further includes
a controller that is configured to
receive fluid pressure data detected by the first pressure sensor and the second pressure sensor, and calculate fluid flow data based on the received fluid pressure data, and
transmit the fluid flow data to the data exchange interface.

12. The system of claim 11 wherein
the infusion line portion includes an infusion line portion valve seat,
the drain line portion includes a drain line portion valve seat,
the second disposable unit includes a pump chamber disposed between the first pressure sensor seat and a region in which the infusion line portion and the drain line portion connect to the patient line portion, and
the fluid exchange device is configured to receive the second disposable unit within the fluid exchange device compartment in a manner such that
an infusion line valve is disposed at a location corresponding to the infusion line portion valve seat,
a drain line valve is disposed at a location corresponding to the drain line portion valve seat, and
a fluid pump is disposed at a location corresponding to the pump chamber, the fluid pump configured to cooperate with the pump chamber to pump fluid within the fluid passageway.

13. The system of claim 11 wherein
the infusion line portion includes an infusion line portion valve seat,
the drain line portion includes a drain line portion valve seat,
the second disposable unit includes a pump chamber disposed between the first pressure sensor seat and a region in which the infusion line portion and the drain line portion connect to the patient line portion, and a pump rotor disposed within the pump chamber, and
the fluid exchange device is configured to receive the second disposable unit within the fluid exchange device compartment in a manner such that
an infusion line valve is disposed at a location corresponding to the infusion line portion valve seat,
a drain line valve is disposed at a location corresponding to the drain line portion valve seat, and
an induction coil is disposed at a location corresponding to the pump chamber, the induction coil configured to drive the pump rotor to pump fluid within the fluid passageway.

14. The system of claim 13 wherein the second disposable unit comprises a bypass passageway that selectively permits fluid flow to be diverted past the pump chamber.

15. The peritoneal dialysis system of claim 13 wherein the second disposable unit comprises a bypass passageway including a first end that communicates with the patient line portion at a location between the pump chamber and the region in which the infusion line portion and the drain line portion connect to the patient line portion, a second end that communicates with the patient line portion at a location between the pump chamber and the first pressure sensor seat, and a bypass valve seat.

16. The peritoneal dialysis system of claim 15 wherein the fluid exchange device comprises a bypass valve at a location corresponding to the bypass valve seat.

17. The peritoneal dialysis system of claim 10 wherein the localized region of reduced fluid passageway diameter includes an orifice plate disposed in the fluid passageway, the orifice plate including an opening having a smaller diameter than inner diameters of portions of the fluid passageway on either side of the orifice plate.

18. The system of claim 1, wherein the transferred patient treatment data is synchronized with patient treatment data of the base peritoneal dialysis system.

19. The system of claim 1, wherein the weight of the peritoneal dialysis fluid exchange system is less than 1 lb.

\* \* \* \* \*